United States Patent [19]
Kirk et al.

[11] Patent Number: 6,025,186
[45] Date of Patent: Feb. 15, 2000

[54] REDUCTION OF MALODOR

[75] Inventors: Ole Kirk, Virum; Charlotte Johansen, Holte; Tomas Tage Hansen, Allerød, all of Denmark

[73] Assignee: Novo Nordisk A/S, Bagsvaerd, Denmark

[21] Appl. No.: 09/133,777

[22] Filed: Aug. 12, 1998

[30] Foreign Application Priority Data

Aug. 14, 1997 [DK] Denmark .................................. 0937/97

[51] Int. Cl.$^7$ ..................................................... C12N 9/08
[52] U.S. Cl. ........................ 435/262; 435/192; 424/94.4; 604/360
[58] Field of Search ........................... 424/94.4; 435/192, 435/262; 604/360

[56] References Cited

U.S. PATENT DOCUMENTS

| | | | |
|---|---|---|---|
| 3,935,862 | 2/1976 | Kraskin | 604/360 |
| 4,385,632 | 5/1983 | Odelhög | 604/360 |
| 4,547,195 | 10/1985 | Jackson | 604/359 |
| 5,389,369 | 2/1995 | Allen | 424/94.4 |
| 5,804,170 | 9/1998 | Negishi et al. | 424/65 |
| 5,866,393 | 2/1999 | Fuglsang et al. | 435/192 |
| 5,888,505 | 3/1999 | Allen | 424/94.4 |

FOREIGN PATENT DOCUMENTS

| | | |
|---|---|---|
| 077651 | 4/1983 | European Pat. Off. . |
| 2104355 | 4/1990 | Japan . |
| 2121665 | 5/1990 | Japan . |
| 6136694 | 5/1994 | Japan . |
| WO 95/04135 | 2/1995 | WIPO . |
| WO 95/27046 | 10/1995 | WIPO . |
| WO 97/02846 | 1/1997 | WIPO . |

*Primary Examiner*—Jon P. Weber
*Attorney, Agent, or Firm*—Steve T. Zelson, Esq.; Reza Green, Esq.

[57] ABSTRACT

The present invention relates to the use of a haloperoxidase in combination with a hydrogen peroxide source for reducing the malodor emanating from soiled hygiene products. The invention also relates to hygiene products with reduced malodor in soiled state.

15 Claims, 3 Drawing Sheets

REDUCTION OF MALODOR

CROSS-REFERENCE TO RELATED APPLICATIONS

This application claims priority under 35 U.S.C. 119 of Danish application serial no. 0937/97 filed Aug. 14, 1997, the contents of which are fully incorporated herein by reference.

FIELD OF THE INVENTION

The present invention relates to the use of a haloperoxidase in combination with a hydrogen peroxide source for reducing the malodour emanating from soiled hygiene products. The invention also relates to hygiene products with reduced malodour in soiled state.

BACKGROUND OF THE INVENTION

It is well established that malodour may be caused by a number of compounds including Volatile Surphuric compounds (VSC), nitrogen containing compounds and short fatty acids.

A source of nitrogen containing compounds, such as ammonia, is urine, faeces and blood giving a bad smell known by most people from either soiled diapers or other hygiene products, such as adult incontinence products, training pants, feminine napkins, tampons and the like.

The bad smell coming from diapers and the like is at least partly a consequence of growth of bacteria, especially *Escherichia coli*, Enterococcus spp. and Proteus spp. present on the skin in the perineum (the region between the anus and the external sexual organs). All strains of Proteus spp. form the enzyme urease during their metabolism. Urease has the ability to rapidly break down urea (constituting about 2% of human urine) into ammonia causing an unpleasant odour.

Removal or Reduction of Malodour in Hygiene Products

A number of odour controlling agent and systems have been described in the literature. For instance, carbon is e.g. in the form of activated carbon well-known for its ability to adsorb odoriferous molecules.

U.S. Pat. No. 5,593,398 discloses protective underwear with malodorous flatus filter comprising activated carbon as the malodour controlling agent.

Zeolitic materials have been shown to be effective against malodour associated with body fluids.

JP patent application no. 02068117 relates to deodorising means e.g. for diapers containing zeolite, copper and activated charcoal.

U.S. Pat. No. 3,903,259 concerns a method of deodorising diapers and human excreta comprising applying to the diapers or the excreta a chemical composition which in its simplest form consists of an acidic material, an antibiotic material, and a solvent. The impregnating composition may also contain a chelating agent and a wetting agent. The treatment of diapers results in a marked decrease in offensive odours from excreta, thus making the changing of sorted diapers less unpleasant.

U.S. Pat. No. 3,935,862 discloses a disposable diaper comprising means for inhibiting ammonia formation therein including an aminopolycarboxylic acid compound in an amount of at least 0.001 g per square inch.

U.S. Pat. No. 4,385,632 concerns a germicidal absorbent body for collecting blood, faeces and urine which contains a water-soluble copper salt which impedes bacterial growth, prevents the breaking down of urea into ammonia and complex-binds ammonia so as to prevent the occurrence of unpleasant odour.

SUMMARY OF THE INVENTION

It is the object of the present invention to provide a hygiene product which in soiled state has a reduced malodour.

In the first aspect the invention relates to the use of a haloperoxidase in combination with a hydrogen peroxide source for reducing the malodour in hygiene products.

In the second aspect the invention relates to hygiene products having a haloperoxidase and a hydrogen peroxide source incorporated e.g. in the absorbing material. Specifically contemplated hygiene product include diapers, adult incontinence products, training pants, feminine napkins, tampons and the like.

DETAILED DESCRIPTION OF THE INVENTION

Figure 1:
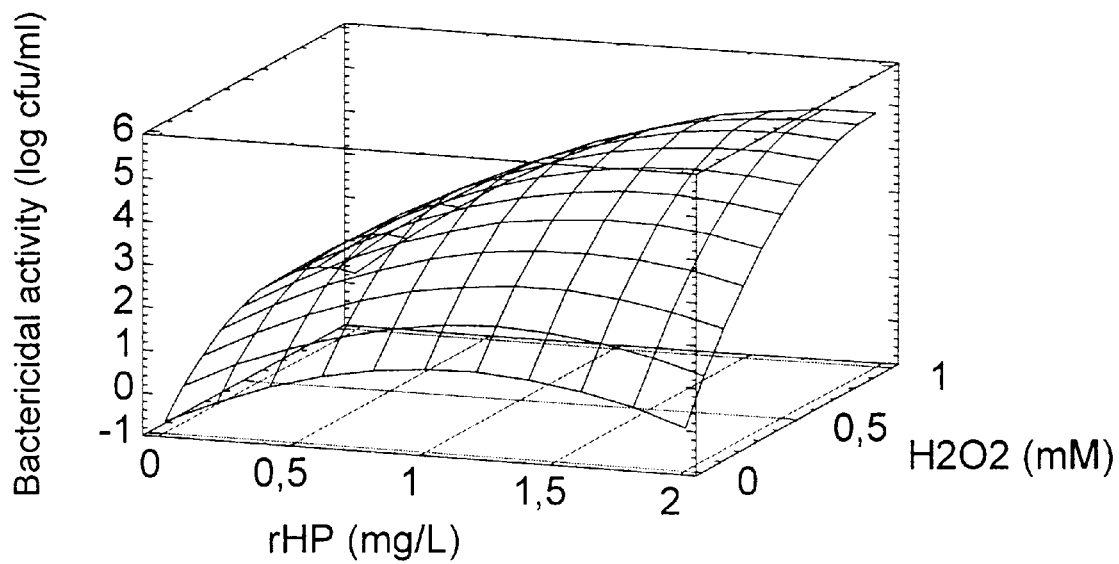
FIG. 1 shows a response surface plot for the antibacterial activity in artificial urine of a Curvularia haloperoxidase (rHP) against a mixed culture of *E. faecalis, E. coli* and *P. mirabilis* adhering to CTMP.

It is the object of the present invention to provide a hygiene product which in soiled state has a reduced malodour.

The term "hygiene product" covers any product suitable for adsorbing or collecting urine, faeces, blood and the like. Examples of hygiene products contemplated are diapers, adult incontinence products, training pants, feminine napkins and tampons.

Hygiene products typically comprise an absorbing material for collecting body fluids and the like. Polyacrylate superabsorbers are often used today. These superabsorbers are capable of absorbing many times their own weight in liquid, such as urine, making it possible to provide thin and less bulky hygiene products capable of holding an increasing amount of liquid before leaking the fluid. These increased amounts of liquid in the hygiene product increase the malodour problem making a solution of the problem more insistent.

In the context of the present invention the term "malodour" means an unpleasant bad smell caused by e.g. nitrogen containing compounds such as ammonia.

The term "absorbing material" covers all kinds of materials capable of holding back liquids.

The inventors have found that haloperoxidases in combination with a hydrogen peroxide source can be used for reducing the malodour of soiled hygiene products.

The term "reducing the malodour" or "reduced malodour" means that the malodour determined by a test panel is assessed to be less pronounced in comparison to a corresponding blind sample.

The bad smell emanating from soiled hygiene products is typically a consequence of nitrogen containing compounds. Urine, faeces, blood and the like are degraded by enzymes produced by bacteria living on the skin covered by the hygiene product. For instance, the enzyme urease, capable of converting urine into ammonia, is produced by bacteria from Proteus spp. living on the skin in the perineum (the region between the anus and the external sexual organs).

In the first aspect the invention relates to the use of a haloperoxidase in combination with hydrogen peroxide source for reducing the malodour of hygiene products.

As will be illustrated in the Examples below a haloperoxidase in combination with a hydrogen peroxide source can be used for significantly reducing the malodour arising in soiled hygiene products by inhibition of the urease activity or by killing or at least inhibiting the growth of microorganisms, such as bacteria, producing compounds, in particular enzymes, responsible for the degradation of urine and the like into bad smelling compounds.

When the haloperoxidase comes in contact with halide ions (especially Cl−) in the urine, the halide ions are oxidised into hypohalous acid (e.g. hypochlorite (i.e. C1O−)) (and probably also other oxidative compounds) which inhibits the activity of urease or is capable of killing or at least inhibiting the growth of microbial cells, such as bacteria cell.

The haloperoxidase may be incorporated into the absorbing material of the hygiene product. A person skilled in the art of hygiene products knows where and how to incorporate the haloperoxidase and the hydrogen peroxide source. The only mandatory criteria is that the haloperoxidase and the hydrogen peroxide are incorporated so that it comes in contact with and can react with halide ions present in e.g. the urine.

Haloperoxidases

Haloperoxidases form a class of enzymes which are able to oxidize halides (Cl−, Br−, I−) in the presence of hydrogen peroxide or a hydrogen peroxide generating system to the corresponding hypohalous acids according to:

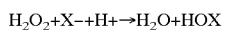

$H_2O_2 + X- + H+ \rightarrow H_2O + HOX$

If a convenient nucleophilic acceptor is present, a reaction will occur with HOX and a halogenated compound will be formed.

There are three types of haloperoxidases, classified according to their specificity for halide ions: Chloroperoxidases (E.C. 1.11.1.10) which catalyse the chlorination, bromination and ionidation of compounds; Bromoperoxidases which show specificity for bromide and iodide ions; and iodoperoxidases (E.C. 1.11.1.8) which solely catalyze the oxidation of iodide ions.

Haloperoxidases have been isolated from various organisms: mammals, marine animals, plants, algae, a lichen, fungi and bacteria (for reference see Biochimica et Biophysica Acta 1161, 1993, pp. 249–256). It is generally accepted that haloperoxidases are the enzymes responsible for the formation of halogenated compounds in nature, although other enzymes may be involved.

Haloperoxidases have been isolated from many different fungi, in particular from the fungus group dematiaceous hyphomycetes, such as Caldariomyces, e.g., *C. fumago*, Alternaria, Curvularia, e.g., *C. verruculosa* and *C. inaequalis*, Drechslera, Ulocladium and Botrytis (see U.S. Pat. No. 4,937,192).

According to the present invention a haloperoxidase obtainable from Curvularia, in particular *C. verruculosa* is preferred such as *C. verruculosa* CBS 147.63 or *C. verruculosa* CBS 444.70. Curvularia haloperoxidase and recombinant production hereof is described in WO 97/04102.

Haloperoxidases have also been isolated from bacteria such as Pseudomonas, e.g., *P. pyrrocinia* (for reference see The Journal of Biological Chemistry 263, 1988, pp. 13725–13732) and Streptomyces, e.g., *S. aureofaciens* (for reference see Structural Biology 1, 1994, pp. 532–537).

Bromide peroxidase has been isolated from algae (see U.S. Pat. No. 4,937,192).

In use, the concentration of the haloperoxidase may be varied in order to achieve the desired effect within the desired time frame. However, according to the invention the haloperoxidase will normally be added in a concentration of 0.01–100 mg enzyme protein per liter, preferably in a concentration of 0.1–50 mg enzyme protein per liter, more preferably in a concentration of 0.2–10 mg enzyme protein per liter.

In a preferred embodiment the haloperoxidase is derivable from Curvularia sp., in particular *C. verruculosa* and *C. inaequalis*.

Hydrogen Peroxide Sources

According to the invention the hydrogen peroxide needed for the reaction with the haloperoxidase may be achieved in many different ways: It may be hydrogen peroxide or a hydrogen peroxide precursor, such as, e.g., percarbonate or perborate, or a peroxycarboxylic acid or a salt thereof, or it may be a hydrogen peroxide generating enzyme system, such as, e.g., an oxidase and its substrate. Useful oxidases may be, e.g., a glucose oxidase, a glycerol oxidase or an amino acid oxidase. An example of an amino acid oxidase is given in WO 94/25574.

It may be advantageous to use enzymatically generated hydrogen peroxide, since this source results in a relatively low concentration of hydrogen peroxide under the biologically relevant conditions. Low concentrations of hydrogen peroxide result in an increase in the rate of haloperoxidase-catalysed reaction.

According to the invention the hydrogen peroxide source needed for the reaction with the haloperoxidase may be added in a concentration corresponding to a hydrogen peroxide concentration in the range of from 0.01–500 mM, preferably in the range of from 0.1–100 mM.

The invention also relates to the hygiene products having incorporated a haloperoxidase and a hydrogen peroxide source e.g. in the absorbing material.

METHODS AND MATERIALS

Materials

Enzymes:

Recombinant haloperoxidase derived from *Curvularia verruculosa* CBS 147.63 (rHP) described in WO 97/04102 (Novo Nordisk)

Recombinant peroxidase derived form *Coprinus cinereus* (rCIP) (available from Novo Nordisk).

Urease Type III from Jack Beans (Sigma No. U 1500)

Artificial Urine A

Urea (300 mM), calcium sulphate (2 mM), magnesium sulphate (3.5 mM), potassium chloride (60 mM) and sodium chloride (130 mM).

Artificial Urine B:

Urea (300 mM), sodium chloride (130 mM), potassium chloride (60 mM), magnesium sulphate (3 mM), calcium sulphate (2.5 mM), Triton X-100 (1 g/l). The artificial urine is made in 10 mM phosphate buffer and adjusted to pH 6.0.

Artificial Urine C:

Made as Artificial Urine B only adding also some amino acids commonly found in human urine: Lysine (0.5 mM), Glycine (2 mM), Alanine (0.5 mM) and Serine (0.5 mM).

Micro-organisms:
*Escherichia coli* (DSM 1576)
*Enterococcus faecalis* (DSM 2570)
*Proteus mirabilis* (DSM 788)

Superabsorbent:

In the examples below the superabsorbent material used was a granular crosslinked sodium polyacrylate polymer obtained from SCA Mölnlycke, Sweden (Batch No. 227131).

Equipment:

Malthus Flexi M2060 (Malthus Instrument Limited)

Methods

Determination of POXU

One POXU is defined as the amount of enzyme which catalyse the conversion of 1 µmol hydrogen peroxide per minute. The activity is measured as oxidation of 2,2'-azinobis [3-ethylbenzothiazoline-6-sulfonate] (ABTS), by monitoring the absorbance at 418 nm at the following conditions: pH 7.0, 30° C., 0.88 mM hydrogen peroxidase, 1.67 mM ABTS and 60 s reaction time.

Malthus-method

The Malthus-method is based on the methods described in Johnston and Jones, (1995), Journal of Microbiological Methods 21, p. 15–26 and Johansen et al. (1995), Journal of Applied Bacteriology 78, p. 297–303.

Determination of haloperoxidase activity

Color reagent:

2.98 g potassium bromide is dissolved in a mixture of 2 ml 0.2% Phenol Read in 96% EtOH and 48 ml 0.3 M TRIS buffer pH 7.0.

Vanadate solution:

18.4 mg sodium orthovanadate is dissolved in 10 ml de-ionized water.

Hydrogen peroxide solution:

0.1 ml 30% hydrogen peroxide is added to 9.9 ml de-ionized water.

When performing the assay, the enzyme sample is preincubated with an amount of the Vanadate solution for a specified period of time and then specified amounts of hydrogen peroxide and the Color Rreagent is added and the activity is monitored by measuring the absorbance at 595 nm (the color changes from read to bluish violet).

Determination of smell:

Evaluation of smell was performed by a test panel of three trained persons.

EXAMPLES

Example 1

Antibacterial Activity of Peroxidase Against *Escherichia coli, Enterococcus faecalis* and *Proteus mirabilis* Attached to Pulp Material The anti-microbial activity of *Cuvularia verruculosa* haloperoxidase was evaluated in artificial urine A against *Escherichia coli* (DSM 1576), *Enterococcus faecalis* (DSM 2570) and *Proteus mirabilis* (DSM 788) adhering to pulp material.

The anti-microbial activity was determined as reduction in living bacterial cells (bactericidal activity) by use of impedance measurements (Malthus).

The detection times measured by the Malthus instrument were converted to cfu/ml by a calibration curve. Either direct or Indirect Malthus measurements were used when enumerating total survival cells (Malthus Flexi M2060, Malthus Instrument Limited). By the direct measurements, the cell metabolism was determined by conductance measurements in the growth substrate.

By the indirect measurements, 3 ml of growth medium was transferred to the outer chamber of the indirect Malthus cells, and 0.5 ml of sterile KOH (0.1 M) was transferred to the inner chamber. The cell suspensions were after enzyme treatment transferred to the outer chamber of the Malthus cell. As cells are growing in the outer chamber they produce $CO_2$ which will dissolve in the KOH in the inner chamber and thereby change the conductance of the KOH. The amount of $CO_2$ formed by the respiring cells surviving the enzyme treatment was used for estimating the number of viable cells. When the conductance change is measurable by the Malthus, a detection time (dt) will be recorded. The dt's were converted to colony counts by use of a calibration curve relating cfu/ml to dt.

The strains were grown in Brain Heart Infusion (BHI) (Oxoid CM 225) until stationary growth phase (30° C., 20 hours), diluted in peptone water and inoculated to chemo-thermo-mechanical-pulp CTMP at the final cell concentration of approximately $10^4$ cfu/0.1 g CTMP. The CTMP was inoculated with either mono-cultures or a mixed culture of the three strains.

The anti-microbial activity of the haloperoxidase (was determined at 35° C. for 30 minutes, by adding the haloperoxidase to the bacterial cells adhering to the CTMP, together with hydrogen peroxide (0.5 mM) and artificial urine. The number of living cells was determined by transfer of the CTMP to Malthus cells.

The activity of the haloperoxidase (0–2 mg enzyme protein/l urine) was evaluated in artificial urine without electron-donor, thus the enzyme activity was initiated by the Cl⁻ in the urine.

The haloperoxidase caused a total kill of the three test organisms; *E. faecalis, E. coli* and *P. mirabilis*.

Furthermore the anti-microbial activity of the haloperoxidase was unchanged in artificial urine compared to a buffer system (pH 6). A total kill of the mixed culture was found at haloperoxidase concentrations above 1.5 mg/l and a hydrogen peroxide concentration above 0.75 mM (FIG. 1).

Example 2

Difference Between the Use of a Peroxidase with Thiocyanate or Iodide as Electron Donor and the Haloperoxidase System.

The antibacterial activity of the haloperoxidase system with chloride from artificial urine A as electron donor (Example 1) and hydrogen peroxide as electron acceptor, was compared with the antibacterial activity of a peroxidase system using either thiocyanate (20 mM) or iodide (1 mM) as electron donor and hydrogen peroxide (0.5 mM) as electron acceptor.

Coprinus peroxidase has antibacterial activity by oxidation of either iodide or thiocyanate. The antibacterial activity was measured by Malthus as described in Example 1, the activity was determined against both planktonic cells suspended in artificial urine and cells on CTMP material. Coprinus peroxidase (Novo Nordisk A/S) (rCIP), with an antibacterial activity comparable to the well-known lactoperoxidase system, was used in concentrations from 0 to 4 POXU/ml.

Figure 2:
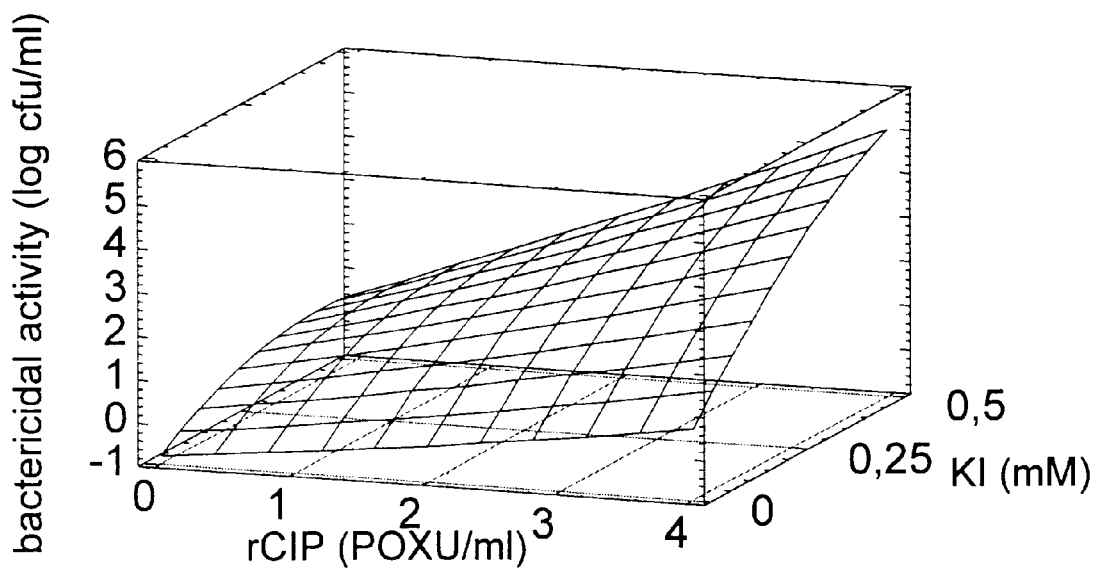
FIG. 2 shows a response surface plot for the antibacterial activity of rCIP and KI ($H_2O_2$=0.5 mM) against *Proteus mirabilis* (planktonic cells).

The rCIP/thiocyanate system was inhibited by the high salt concentration in the artificial urine whereas the rCIP/iodide systems was found active in artificial urine (FIG. 2).

Figure 3:
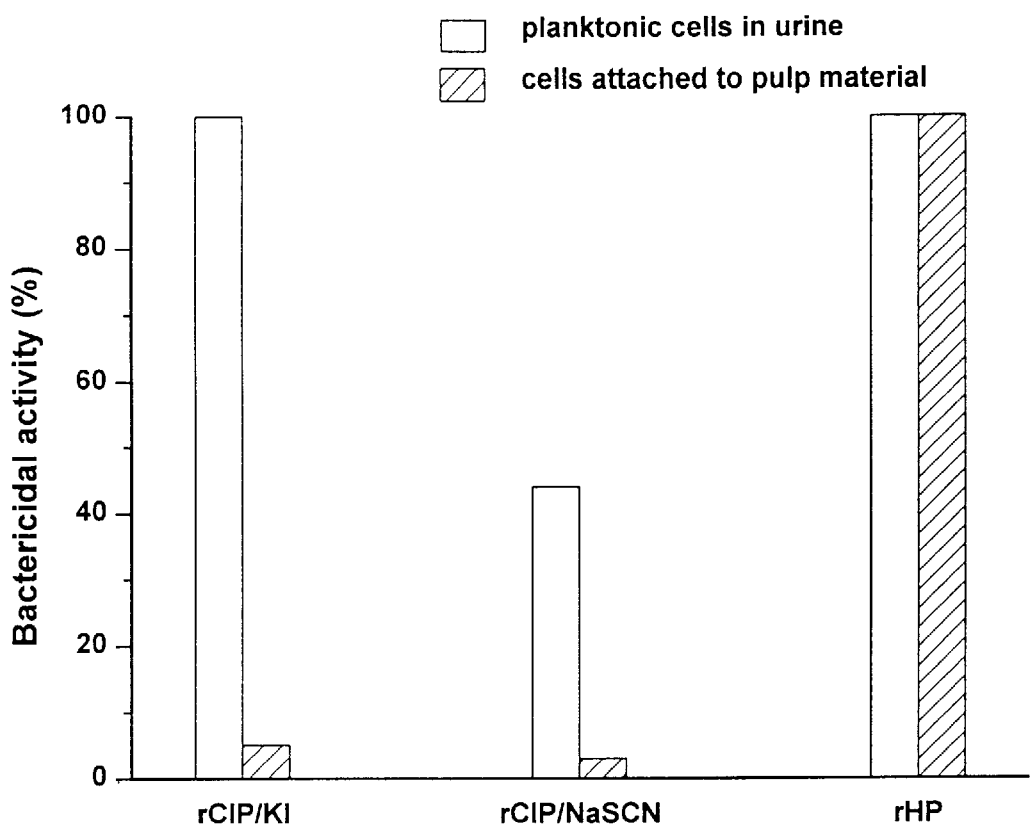
FIG. 3 shows the bactericidal activity of rCIP/KI, rCIP/NaSCN and haloperoxidase (rHP) against *P. mirabilis* in artificial urine. Cells were either suspended (planktonic) in artificial urine or adhering to CTMP.

However, both thiocyanate and iodide based systems were significantly inhibited if CTMP was present in the artificial urine (FIG. 3) due to interactions between the pulp material and thiocyanate and iodide, respectively, thus these systems have increased activity in the CTMP material used in nappies.

The haloperoxidase system was not inhibited by the CTMP material (FIGS. 1 and 3) as a total kill of the bacteria on CTMP was measured.

Example 3
Inhibition of Malodour Formation by Inhibiting Urease Using a Haloperoxidase Experiments were performed using 10 ml Artificial Urine B. Initially, hydrogen peroxide was added to a final concentration of 1 mM and then recombinant *Curvularia verruculosa* haloperoxidase was added to the desired concentration.

The experiments were initiated by addition of Urease. Samples were incubated on a shaking water bath at 25° C. in closed vessels.

Urease activity in the samples was evaluated at given time intervals by monitoring pH (using a Radiometer PHM 85 precision pH Meter) and production of ammonia monitored by the development of the characteristic malodour.

Results:

TABLE 1

| Haloperoxidase (mg/l) | Urease (U/ml) | pH at 15 min | Smell at 15 min | pH at 45 min |
|---|---|---|---|---|
| 0 | 10 | 8.5 | Strong | 8.8 |
| 0.1 | 10 | 8.4 | Strong | 8.7 |
| 0.5 | 10 | 6.2 | None | 6.2 |
| 1.0 | 10 | 6.0 | None | 6.0 |

This example clearly illustrates that the haloperoxidase/$H_2O_2$ system is capable, in a dose dependent manner, of completely inactivating Urease and thereby prevent the development of malodour from the samples.

Example 4
Immobilization of Haloperoxidase on a Superabsorbent Polymer:

2 ml of a solution of recombinant *Cuvularia verrucolosa* haloperoxidase (0.375 mg/ml) was added drop-wise to 20 g vigorously stirred superabsorbent polymer in a glass beaker. Then, water was removed by drying the material overnight in a vacuum oven at 25° C.

The activity of the immobilized haloperoxidase was monitored by adding 80 µl Vanadate solution to 100 mg of the superabsorber followed by vigorous mixing on a Whirl mixer.

One minute later, 80 µl color solution and 80 µl hydrogen peroxide solution was added and the sample was mixed again. In a blank sample of the neat superabsorbent polymer the color remained bright yellow while the color quickly changed to dark purple in the sample containing immobilized haloperoxidase.

The immobilized haloperoxidase preparation was split into two equivalent samples and one was stored at 5° C. while the other was stored at room temperature.

After 10 days the activities of the two samples were assayed as above and no visual difference was observed neither between the samples not to the sample assayed immediately after immobilization.

The activity was also monitored using a slightly modified activity assay in which the Color Reagent was made using Artificial Urine C in stead of 0.3 MTRIS buffer pH 7. In this case, the Color Reagent has a bright yellow color but the same dark purple color was developed when added to the immobilized haloperoxidase sample when performing the assay.

This example shows that haloperoxidase can be efficiently immobilized on the superabsorbent polymer used in hygienic products. Furthermore, the immobilized enzyme has activity also in the presence of Artificial Urine and exhibits high stability even at room temperature.

Example 5
Inhibiting Maldour Formation Using Immobilized Haloperoxidase.

The ability of immobilized haloperoxidase to inactivate Urease and thereby inhibit malodour formation was monitored by using 100 mg superabsorbent either neat or with immobilized haloperoxidase (as prepared in Example 4).

The samples were either mixed thoroughly with 5 mg sodium perborate trihydrate (Merck, Art. 1.06560.) and then added 100 µl Artificial Urine C or the samples were added 1000 µl Artificial Urine C mixed with 125 µl 0.3% hydrogen peroxide.

Following vigorously mixing on a Whirl mixer 500 µl a solution of Urease (10 U/ml) was immediately added followed by mixing again.

The samples were incubated on a shaking water bath at 25° C. in closed vessels and Urease activity was monitored at given time intervals by monitoring pH in the samples by contacting a small part of the sample with pH indicator strips (Merck Neutralit pH 5–10; Art. 1-09533.) and by evaluating production of ammonia by monitoring the characteristic malodour.

Results:

TABLE 2

| Haloperoxidase added to SAP | Perborate addition | $H_2O_2$ addition | After 5 min | | After 30 min | |
|---|---|---|---|---|---|---|
| | | | pH | Smell | pH | Smell |
| − | − | − | 7.5 | faint | 9 | strong |
| − | + | − | 6.5 | faint | 9 | medium |
| + | − | − | 8 | faint | 9 | strong |
| + | + | − | 6 | none | 6 | none |
| + | − | + | 6 | none | 6 | none |

This example clearly demonstrates that haloperoxidase immobilized on a superabsorbent polymer in combination with hydrogen peroxide is capable of completely preventing the formation of malodour which is normally the result of Urease action on urine.

The example also demonstrates that hydrogen peroxide can be conveniently added to the system in the form of the solid sodium perborate.

We claim:

1. A method for reducing malodor in a hygiene product containing absorbent material, said method comprising incorporating into said product a haloperoxidase and a hydrogen peroxide source.

2. A method as defined in claim 1, wherein said haloperoxidase is derived from bacteria, fungi, or algae.

3. A method as defined in claim 2, wherein said haloperoxidase is derived from a fungus selected from the group consisting of Caldariomyces, Alternaria, Curvularia, Drechslera, Ulocladium, and Botrytis.

4. A method as defined in claim 3, wherein said haloperoxidase is derived from *Curvularia verruculosa* CBS 147.63.

5. A method as defined in claim 2, wherein said haloperoxidase is derived from a bacterium selected from the group consisting of Pseudomonas and Streptomyces.

6. A method as defined in claim 1, wherein said hydrogen peroxide source is selected from the group consisting of hydrogen peroxide and a hydrogen peroxide precursor.

7. A method as defined in claim 1, wherein said hygiene product is selected from the group consisting of a diaper, training pants, an adult incontinence product, a feminine napkin, and a tampon.

8. A hygiene product containing absorbent material, said product comprising haloperoxidase and a hydrogen peroxide source.

9. A hygiene product as defined in claim 8, wherein said haloperoxidase and hydrogen peroxide source are incorporated into said absorbent material of said product.

10. A hygiene product as defined in claim 8, selected from the group consisting of a diaper, training pants, an adult incontinence product, a feminine napkin, and a tampon.

11. A hygiene product as defined in claim 8, wherein said haloperoxidase is derived from bacteria, fungi, or algae.

12. A hygiene product as defined in claim 11, wherein said haloperoxidase is derived from a fungus selected from the group consisting of Caldariomyces, Alternaria, Curvularia, Drechslera, Ulocladium, and Botrytis.

13. A hygiene product as defined in claim 12, wherein said haloperoxidase is derived from *Curvularia verruculosa* CBS 147.63.

14. A hygiene product as defined in claim 11, wherein said haloperoxidase is derived from a bacterium selected from the group consisting of Pseudomonas and Streptomyces.

15. A hygiene product as defined in claim 8, wherein said hydrogen peroxide source is selected from the group consisting of hydrogen peroxide and a hydrogen peroxide precursor.

* * * * *